Figure 1:
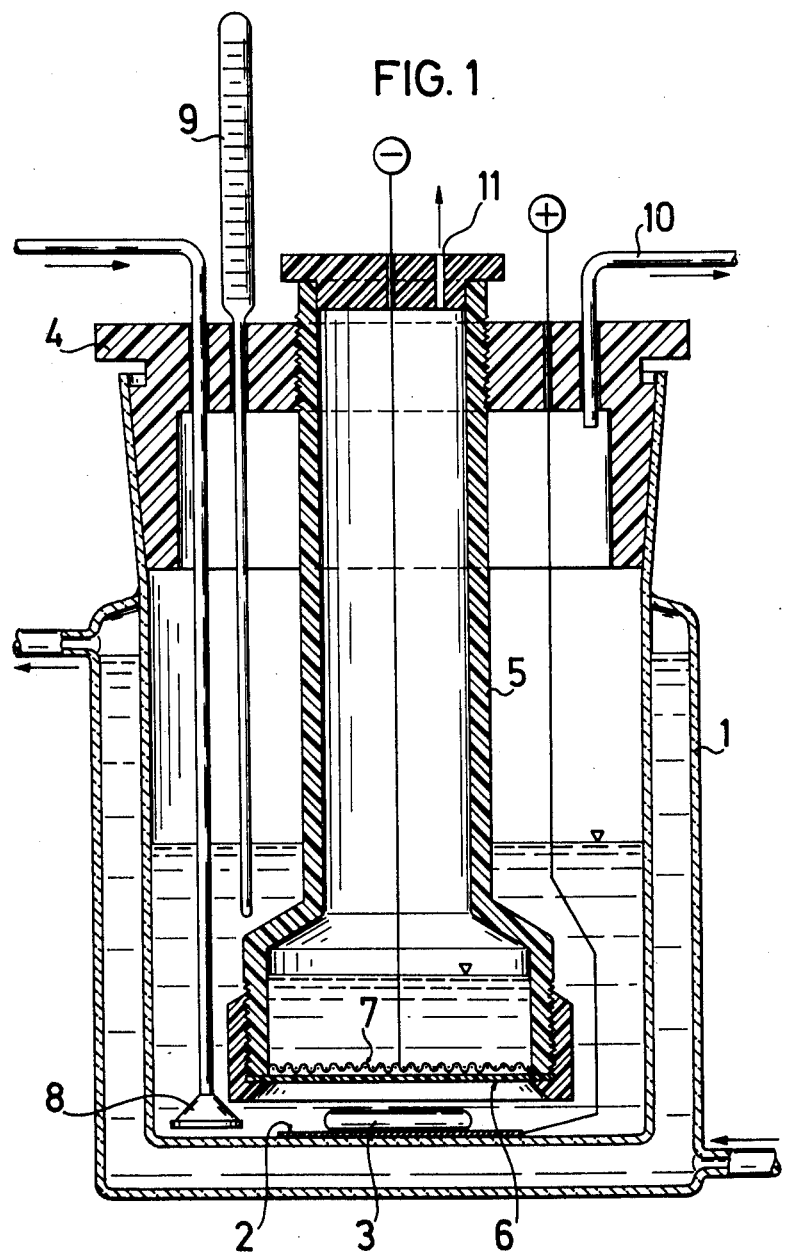

United States Patent [19]

Millauer

[11] 4,014,762
[45] Mar. 29, 1977

[54] PROCESS FOR THE PREPARATION OF HEXAFLUOROPROPENE EPOXIDE

[75] Inventor: Hans Millauer, Eschborn, Taunus, Germany

[73] Assignee: Hoechst Aktiengesellschaft, Frankfurt am Main, Germany

[22] Filed: Dec. 18, 1975

[21] Appl. No.: 641,930

[30] Foreign Application Priority Data

Dec. 20, 1974 Germany .......................... 2460468

[52] U.S. Cl. .................................................. 204/79
[51] Int. Cl.² .......................................... C25B 3/02
[58] Field of Search ................................ 204/79, 59

[56] References Cited

UNITED STATES PATENTS 3,342,717  9/1967  Leduc ................................ 204/265

*Primary Examiner*—R. L. Andrews
*Attorney, Agent, or Firm*—Curtis, Morris & Safford

[57] ABSTRACT

Hexafluoropropene epoxide

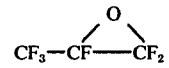

is prepared by anodic oxidation of hexafluoropropene in an electrolytical cell which contains at least in the anode space as electrolyte a solution of the following composition: glacial acetic acid and/or acetonitrile with from 2 – 40% by volume of water and about 1 – 10 weight % — calculated on the total solution — of at least one alkali perchlorate, -hexafluorosilicate, -tetrafluoroborate, -hexafluorophosphate or -nitrate and/or of at least one of the free acids on which these salts are based as compounds emphasizing the conductance. The anode consists of a metal of the platinum group of the periodical table or of an alloy of these metals or of $PbO_2$, the cathode consisting of one of the usual metals or of graphite. If cathode space and anode space are separated, catholyte and anolyte are either of the same kind or the catholyte is one of the usual electrolytes. The cell temperature should range from about −30 to +50° C. Hexafluoropropene epoxide is employed for preparing polymers which are especially important as inert liquids, lubricant liquids and hydraulic liquids.

3 Claims, 3 Drawing Figures

PROCESS FOR THE PREPARATION OF HEXAFLUOROPROPENE EPOXIDE

The present invention is related to the preparation of hexafluoropropene epoxide

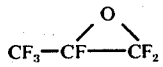

by anodic oxidation of hexafluoropropene.

Various chemical processes are known already for preparing hexafluoropropene epoxide. One possible method for obtaining hexafluoropropene epoxide is reaction of hexafluoropropene with hydrogen peroxide in aqueous-methanolic potassium hydroxide solution at from −40° to −50° C according to U.S. Pat. No. 3,358,003. In order to obtain satisfactory yields according to this process, it is essential to employ a multiple excess quantity of oxidation agent. However, a translation of the exothermic process to an industrial scale involves considerable difficulties and risks.

According to another process which has been described in French Pat. No. 1,416,957, hexafluoropropene epoxide may be prepared by oxidation of hexafluoropropene with oxygen at an elevated temperature and under elevated pressure - reaction conditions, which favor the formation of numerous by-products.

A disadvantage, which is common to all known chemical methods for preparing hexafluoropropene epoxide, arises out of its tremendous instability in the corresponding reaction mixtures or rather under the reaction conditions applied, since hexafluoropropene epoxide gives way most easily under nucleophile or electrophile attacks to transpositions or other alterations. If the preparation takes place in basic reaction media, the starting material hexafluoropropene may be consumed by secondary reactions.

Further difficulties and risks for the execution of the chemical preparation process result from the necessity of controlling the oxidation power of the chemical oxidation agent employed, especially if considerable excess quantities are utilized.

The electrochemical preparation of epoxides is known so far only in respect to alkenes which are little or not at all substituted, i.e. rich in hydrogen.

Thus, the German Pat. Nos. 1,252,649, 1,258,856 and 1,258,857 and the U.S. Pat. Nos. 3,288,692 and 3,342,717 — for example — describe electrochemical processes for preparing alkene epoxides, wherein the solution of a metal halide in an electrochemical cell is electrolyzed in the presence of an olefin, anodically formed halogen after reaction with water being added as hypohalous acid to the olefin and subsequently the thus formed halohydrin is dehydrohalogenated to form the epoxide by means of dehydrohalogenation the cathodically formed metal hydroxide.

This group of processes is not suitable for the preparation of hexafluoropropene-epoxide, because so far no attempt to add hypohalous acids to hexafluoropropene has been successful.

The German Offenlegungsschrift No. 2,057,519 describes an electrochemical process for preparing alkene epoxides, preferably propene epoxide, whereby a contact is established between the olefin and an anode liquid which is obtained by means of electroylsis of an aqueous solution containing acetate ions. According to the Examples specified in the disclosure, the described process takes place in the presence of copper, cobalt, thallium or silver acetate; it is also possible to add complex-forming substances such as pyridine. This process has the great disadvantage that the incomplete selectivity of the usual membranes is responsible for a constant loss in heavy metal ions due to their migration into the cathode space and that no means have been found so far to prevent these losses. If this process is applied to to perfluoropropene, no epoxide is obtained.

In accordance with German Auslegeschrift No. 1,906,182 the preparation of epoxides from monoolefins may be carried out in such a way that in an electrochemical cell aqueous electrolytes are submitted to such conditions that molecular or nascent oxygen is formed as main product and that a monoolefin is introduced into the cell at a temperature of at least 24° C, at a spot close to the anode surface. Though this German Auslegeschrift states that this method also allows for anodically oxidizing monoolefins to yield the corresponding epoxides which are substituted by halides such as F or Cl, a test run of this process with hexafluoropropene as starting material showed that no formation of hexafluoropropene epoxide took place.

Therefore, it is an object of the present invention to provide a process for the electrochemical oxidation of hexafluoropropene which gives a good yield of hexafluoropropene epoxide.

The present invention solves this problem by submitting hexafluoropropene to anodic oxidation in an electrolysis cell which contains at least in the anode space as electrolyte a solution consisting of glacial acetic acid and/or acetonitrile with about 2 – 40% by volume of water and about 1 – 10 weight % — calculated on the total solution — of at least one alkali perchlorate, alkali hexafluorosilicate, alkali tetrafluoroborate, alkali hexafluorophosphate or alkali nitrate and/or at least one of the free acids on which these salts are based as compositions for improving the conductance, the anode consisting of a metal of the platinum group of the periodic table (Ir, Pt) or of its alloys or of $PbO_2$ the cathode consisting of one of the usual metals or of graphite, the catholyte, provided that cathode space and anode space be separate, being of the same nature as the anolyte, or the catholyte being another of the usual electrolytes, and the cell being maintained at a temperature of from about −30° to +50° C, preferably of from about 0° to 30° C.

The anodic oxidation process according to the invention may be carried out either in a non-separated cell, or preferably in a cell which is separated by one of the conventional diaphragms, especially by a ion -exchange-membrane to establish a cathode space and an anode space. The construction of this cell is not of critical importance, the oxidation may be carried out e.g. even in a simple glass tube. Nor is the cathode material of critical importance; it is preferably copper, nickel, steel or graphite. If the electrode chambers of the cell are separated, the catholyte is not critically important either; the catholyte may be of the same kind as the anolyte or may as well consist of one of the usual electrolyte solutions such as water and the conducting salts of the anolyte.

If a composition other than that of the anolyte is used, special attention must be paid to prevention of intermixing with the anolyte, by suitable diaphragms, especially ion-exchange-membranes.

Critically important is the composition of the anolyte which may consist of an organic solvent selected from the group consisting of acetic acid and acetonitrile containing about 2 to 40% by volume, preferably about 5 to 10% by volume of water — calculated on the total solution. As suitable compositions for improving the conductance, i.e. compositions facilitating the flow of current, only a few need be cited. Especially suitable are alkali (Li, Na, K, Rb, Cs) perchlorates, alkali hexafluorosilicates, alkali tetrafluoroborates, alkali hexafluorophosphates and nitrates, as well as the free acids on which these salts are based. Each one of these compositions may be employed either alone or blended with one or several of any of the other compounds mentioned. Special preference is given to the use of Na-perchlorate, Na tetrafluoroborate, Na hexafluorophosphate and Na nitrate and to the free acids on which these salts are based.

Surprisingly, the number of conducting compounds suitable to the process according in the invention, is quite limited. When employing cathodically reducible conducting salts such as those with $NO_3$ ions, separated electrolysis cells are convenient.

The pH of the anolyte varies from about 7 down to about O, preferably from about 6 to about 1.

The construction of the anode has to be adapted to the heterogeneous reaction, i.e. the anode should have a large surface easily accessible to the gaseous component, such as sheets, nets or plates. When using $PbO_2$ especially suitable embodiments are coatings on a conducting basic material, especially graphite or titanium. Preference is given to the use of anodes which have been prepared as metal sheets from the electrode materials as per the invention. Suitable current densities per $dm^2$ of the anode surface may be chosen from the usual range of about 0.5 to about 15 $A/dm^2$, preferably about 1 $A/dm^2$ to 10 $A/dm^2$. The cell voltage results from the amperage, the conductance and the geometric dimensions of the cell, being generally about from 4 to 30 Volt.

The quantity of perfluoropropene fed to the anode may be e.g. equivalent to the quantity of applied current, i.e. 0.5 mole of hexafluoropropene per Faraday (26,8 A/h). The use 70% to 200%, especially from 80 to 150% of this equivalent is quantity is preferred. The reaction mixture which consists in perfluoropropene and perfluoropropene epoxide, may be recycled entirely or partially in known manner. A complete conversion is not required, since mixtures of perfluoropropene and perfluoropropene epoxide are suitable as well.

The electrolysis may be carried out either under normal pressure, or also under elevated pressure, provided that under the reaction conditions the perfluoropropene be in its gaseous state, i.e. preferably under pressures of up to about 5 bar.

Perfluoropropene epoxide or its mixtures with perfluoropropene are the starting materials for the homopolymerization or copolymerization in known manner to yield perfluoropolyethers, which have become more and more important as inert liquids, lubricant liquids or hydraulic liquids.

Figure 2:
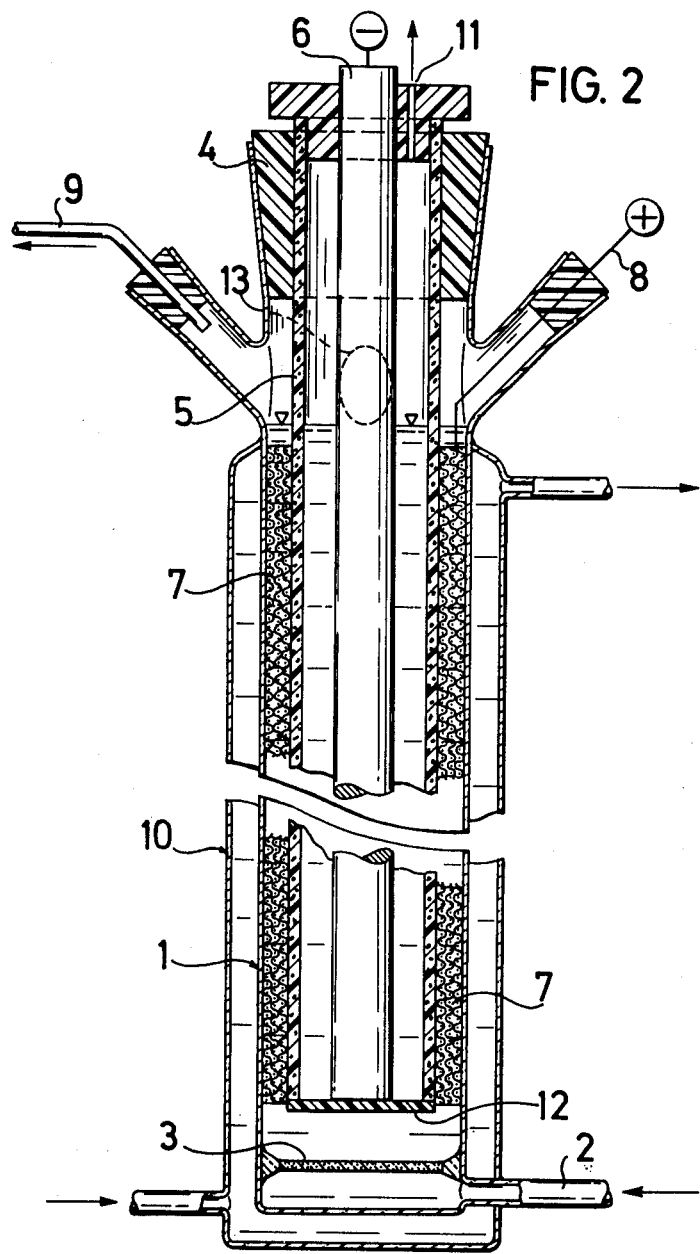
Figure 3:
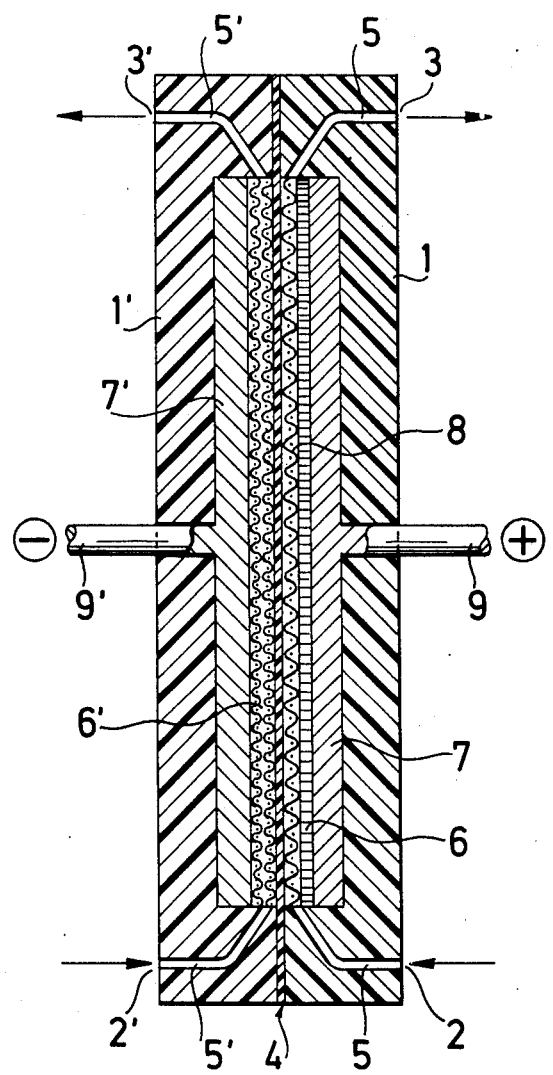

FIGS. 1, 2, and 3 represent vertical cross sections of specific embodiments of the invention.

The following Examples and drawings illustrate the invention:

EXAMPLE 1

A platinum sheet (50 × 50 mm) which acts as anode 2 is placed horizontally on the bottom of a beaker-like cell (FIG. 1) having an inside diameter of 100 mm and a height of 150 mm and equipped with an outer cooling jacket 1. A magnetic agitator 3 of 30 mm length is laid onto the platinum sheet. The cover of the cell consists in a polyethylene stopper 4 which is pierced by several drilled openings. A tube 5 having an inside diameter of 30 mm and made of polyethylene is threaded into the central opening. The tube widens at its lower tip to 54 mm and is closed there by means of a horizontally placed ion exchanger membrane 6 (made of Nafion$^{(R)}$ XR 475; $F = 23$ cm$^2$) A copper net ($F = 23$ cm$^2$) also placed horizontally in the thus formed cathode space, acts as cathode 7. The distance from anode to cathode is about 30 mm. A gas inlet tube with frit 8 is introduced through the cover and reaches almost down to the bottom of the cell. Further drilled openings in the cell cover bear a thermometer 9 and discharge 10 the gas escaping from the anode space. The cathodically formed hydrogen escapes through the opening 11.

200 ml of an electrolyte composed of acetonitrile (nine parts by volume), water (one part by volume) and sodium perchlorate (50 g/l), are charged into the anode space. In the cathode space is present a solution of 5 g of sodium perchlorate in 100 ml of water. A hexafluoropropene stream is then introduced at a speed of about 5 g/h, controlled by a rotameter, while agitating. Simultaneously a direct current of 2 A (corresponding to a current density of 80 mA/cm$^2$; the required cell voltage of 5 – 7 V) is led through the cell. The water concentration of the anolyte is maintained by adding 0.67 ml of $H_2O$ per hour.

The reaction temperature is 0° C. The gases flowing from the anode space are washed with water in a wash bottle, dried with calcium chloride in a tubular drying device and subsequently led into a cooling trap at −78° C.

After having reached stable test conditions (about 4 hours after the start of the test), about 4 g of the condensation product per hour are collected in the cooling trap, this product consisting of 71% of hexafluoropropene and of 28% of hexafluoropropene epoxide according to a gaschromatographical analysis.

This result represents a material efficiency of about 52%, calculated on the reacted hexafluoropropene, and a current efficiency of 18%.

EXAMPLE 2

The electrochemical cell (FIG. 2) consists of an upright cylindrical glass tube 1 of about 280 mm total length and an inside diameter of 40 mm. Inlet 2 for the hexafluoropropene is positioned close on top of the cell bottom, the hexafluoropropene entering the cell through a glass frit 3. The top opening of the cylindrical glass tube is equipped with a standard ground joint sleeve (NS 40), in which is fitted a stopper of polyethylene 4. A cylinder 5 of porous polyethylene (length 250 mm, outer diameter 30 mm, thickness of wall 2.5 mm, volume of the pores about 45%) is introduced through a central drilled opening of this stopper, the cylinder extending concentrically into the glass cylinder unto a depth of about 10 mm above the glass frit. The lower tip of this cylinder is shut by a circular-shaped polyethylene plate 12. The thus formed interior space of the polyethylene cylinder represents the cathode space of the cell. At the interior of this cathode space is as cathode 6 a nickel rod (length 280 mm, diameter 12 mm) which reaches down to the bottom of the polyethylene cylinder.

The concentric annular clearance of about 5 mm width, which is formed by the polyethylene cylinder and the outer glass cylinder, represents the anode space.

A platinum net with 10% of iridium (length 250 mm, width 200 mm, wire thickness 0.12 mm, 250 meshes/cm$^2$) functions as anode 7, the described net being shaped as a roll and placed in the annular clearance at the height of 200 mm. The anode current supply 8 takes place through further ground glass openings (NS 14) positioned laterally at the top end of the cell above the level of the elctroyte, where the thermometer 13 and the outlet 9 for gaseous substances escaping from the anode space are also positioned. The cathodicallly formed hydrogen escapes through opening 11.

The cell is charged with about 200 ml of an electrolyte having the following composition: acetonitrile (nine parts by volume), water (one part by volume) and sodium tetrafluoroborate (50 gl/l). A hexafluoropropene current which is controlled by a rotameter is led through the anode space from the bottom to the top at a rate of about 7 g/h. A direct current of 3 A, equivalent to a current density of 6 mA/cm$^2$, is simultaneously led through the cell; the cell voltage required on this purpose is 5 – 7 V. 1.0 ml of fresh water per hour is added to the anolyte.

The temperature of the anolyte is maintained at of about 20° – 25° C by temperature control of the cooling water. The gases which flow from the anode space are washed with water in a washing bottle and conveyed to a cooling trap at −78° C.

After having reached stable test conditions (about 5 hours after the start of the test), about 5 g of a condensation product per hour are obtained in the cooling trap, this product being composed — as per gaschromatographical analysis — of 53% of hexafluoropropene and 46% of hexafluoropropene epoxide. These figures represent a material efficiency of about 45%, calculated on the hexafluoropropene participating in the reaction, and a current efficiency of 25%.

EXAMPLE 3

The operational method is identical to that of example 2, but the electrolyte employed has the following composition: glacial acetic acid (17 parts by volume), water (two parts by volume) and 65% nitric acid (one part by volume). At a cell current of 3 A the required cell voltage ranges from 6 – 8 V.

The yield in condensation product per hour is about 6 g, the product being composed — as per gaschromatographical analysis — of 63% of hexafluoropropene and 36% of hexafluoropropene epoxide. These figures represent a material efficiency of about 60%, calculated on the hexafluoropropene having participated in the reaction, and a current efficiency of 23%.

EXAMPLE 4

The operational method is identical to that of example 2, the cell is however operated without diaphragm (not separated) and an electrolyte is employed having the following composition: acetonitrile (nine parts by volume), water (one part by volume) and borofluohydric acid (50 g/l). At a cell current of 3 A the required cell voltage ranges from 6 – 8 V. The condensation product is obtained at a yield per hour of about 4.9 g, the product consisting — as per gaschromatographical analysis — of 50% of hexafluoropropene and 49% of hexafluoropropene epoxide. These figures represent a material efficiency of 48%, calculated on the hexafluoropropene having participated in the reaction, and a current efficiency of 26%.

EXAMPLE 5

A divided circulation cell (FIG. 3) is utilized for carrying out the following test example. The cell body consists of two shell halves 1,1', each having an inlet 2 and an outlet 3 for the anolyte, and an inlet 2' and an outlet 3' for the catholyte, clamped between the two shell halves there is a diaphragm 4 consisting of a cation exchange membrane (Nafion X R 475). The anode space and the cathode space of the cell are each encased by the diaphragm and one shell half. The anolyte enters the cell through lower passage 5, flows over the anode 6 and leaves through the upper passage 5. The catholyte enters the cell through the lower passage 5', flows through the net-like cathode 6' and out through the upper passage 5'. The anolyte and catholyte are uniformly distributed in the anolyte and catholyte chambers respectively. The anode 6 consists of a layer of lead dioxide (PbO$_2$) which is applied electrolytically onto the carrier 7 consisting itself of graphite. The cathode 6' consists of a net made of chromium-nickel-molybdenum steel welded spotwise on a carrier plate 7' made of the same material. The cathode net 6' adheres tightly to the diaphragm.

Inside the anode space a thin net 8 is employed as spacer between the anode and the diaphragm. The power is supplied through the contact rods 9 and 9'. The electrodes have the dimensions 140 × 140 mm ($F$ = about 200 cm$^2$).

The circulation cell is provided with two external electrolyte circuits (not shown).

The anolyte circuit is composed of a centrifugal pump set up ahead of the cell inlet at the side of the anode (throughput of the pump 200 to 400 l·h$^{-1}$). Perfluoropropene is introduced into the anolyte at the suction end of the pump (30 g·h$^{-1}$), this anolyte at the beginning of the test being composed of 1700 g of glacial acetic acid, 235 g of water and 65 g of nitric acid (HNO$_3$). The anolyte stream leaving the cell is conducted to a coolable degasification tower, at the upper end of which the gaseous reaction products and that part of the perfluoropropene which has not participated in the reaction are removed from the circuit, whilst the anolyte, including the dissolved portions of reaction products and perfluoropropene, replenished by fresh perfluoropropene, is fed back to the anode chamber of the cell. The anolyte is maintained at a temperature of from 10° to 20° C.

The catholyte circuit is set up as follows: the catholyte which consists at the beginning of the test of 400 g of glacial acetic acid and 100 g of water, is conducted through the cathode space of the cell by means of a centrifugal pump (throughput 20 – 40 l·h$^{-1}$), there charged with the cathodically formed hydrogen and led into a gas separator; after separation of the hydrogen the catholyte is fed back into the cathode chamber of the cell.

The circulation cell is operated with a direct current of 5 A (25 mA·cm$^{-2}$); the required cell voltage amounts to 6–8 V.

The concentration of water in the anolyte is maintained at about from 10–15 weight % by addition of fresh water (about 1 g·h$^{-1}$). The volume increase of the catholyte, due to the migration of electrolyte components through the diaphragm, is compensated by recycling a portion of the catholyte (about 10 g·h$^{-1}$) into the anode cycle.

During a test period of 24 operating hours, there are introduced 720 g (4.80 moles) of perfluoropropene. The discharged gaseous reaction products and unreacted in the reaction are washed in a washing tower with cool 40% aqueous potassium hydroxide solution, led through a drying tower with calcium chloride and subsequently condensed in a cooling trap at − 78° C. 670 g of a condensate are obtained consisting, as per gaschromatographical analysis, of 19% of perfluoropropene epoxide and about 80% of perfluoropropene. These values represent a material yield of about 65%, calculated on reacted perfluoropropene. The current efficiency amounts to 34% of the theoretical yield.

If pure perfluoropropene is replaced as starting substance by a mixture of about 80% of perfluoropropene and about 20% of perfluoropropene epoxide, while proceeding as described above, a condensate is obtained which consists of about 36% of perfluoropropene epoxide and about 64% of perfluoropropene.

What is claimed is:

1. A process for preparing hexafluoropropane epoxide by oxidation of hexafluoropropene, which comprises submitting hexafluoropropene to anodic oxidation in an electrolytic cell having an anode space containing an electrolyte consisting essentially of a solution of glacial acetic acid and/or of acetonitrile with from about 2–40% by volume of water and about 1–10 weight %, calculated on the total solution, of at least one compound for improving the conductivity of the electrolyte, said compound being selected from alkali perchlorates, hexafluorosilicates, tetrafluoroborates, hexafluorophosphates nitrates, the free acids of such salts and mixtures of such compounds, the anode being composed of a metal of the platinum group or of its alloys or of PbO$_2$, the cathode being composed of a metal or graphite, and the cell being maintained at a temperature of from about −30° to +50° C.

2. A process according to claim 1, which comprises using as the compound improving the conductivity of the electrolyte is selected from sodium perchlorate, sodium tetrafluoroborate, sodium hexafluorophosphate and sodium nitrate, the free acids of these salts and mixtures of such compounds.

3. A process according to claim 1 which comprises maintaining the cell at a temperature of about 0° to 30° C.

* * * * *